US009615937B2

(12) United States Patent
Barreiro

(10) Patent No.: US 9,615,937 B2
(45) Date of Patent: Apr. 11, 2017

(54) LATERAL APPROACH EXPANDABLE SPINAL IMPLANT AND METHOD

(71) Applicant: SPINE WAVE, INC., Shelton, CT (US)

(72) Inventor: Peter Barreiro, West Haven, CT (US)

(73) Assignee: Spine Wave, Inc., Shelton, CT (US)

( * ) Notice: Subject to any disclaimer, the term of this patent is extended or adjusted under 35 U.S.C. 154(b) by 0 days.

(21) Appl. No.: 14/941,749

(22) Filed: Nov. 16, 2015

(65) Prior Publication Data

US 2016/0166399 A1 Jun. 16, 2016

Related U.S. Application Data

(62) Division of application No. 14/342,563, filed as application No. PCT/US2012/054055 on Sep. 7, 2012, now abandoned.

(Continued)

(51) Int. Cl.
*A61F 2/44* (2006.01)
*A61F 2/46* (2006.01)

(Continued)

(52) U.S. Cl.
CPC ............ *A61F 2/447* (2013.01); *A61F 2/4455* (2013.01); *A61F 2/4601* (2013.01); *A61F 2/4611* (2013.01); *A61B 2017/0256* (2013.01); *A61F 2/4465* (2013.01); *A61F 2002/2835* (2013.01); *A61F 2002/305* (2013.01); *A61F 2002/3008* (2013.01); *A61F 2002/3052* (2013.01); *A61F 2002/30383* (2013.01); *A61F 2002/30504* (2013.01); *A61F 2002/30556* (2013.01); *A61F 2002/30579* (2013.01); *A61F 2002/30599* (2013.01); *A61F 2002/30601* (2013.01);

(Continued)

(58) Field of Classification Search
CPC ...................................................... A61F 2/447
See application file for complete search history.

(56) References Cited

U.S. PATENT DOCUMENTS 4,545,374 A * 10/1985 Jacobson .......... A61B 17/0218 600/210
4,873,746 A 10/1989 Scheier et al.

(Continued)

FOREIGN PATENT DOCUMENTS

SU 1650114 A1 5/1991
WO 0044319 8/2000

OTHER PUBLICATIONS

Nuvasive. Creative Spine Technology; "A Material You Can't. The CoRoent Family of Radiolucent Systems."; 2004; USA.

(Continued)

*Primary Examiner* — Jan Christopher Merene
(74) *Attorney, Agent, or Firm* — Hoffmann & Baron, LLP

(57) ABSTRACT

An expandable interbody fusion device configured for placement into the intradiscal space between vertebral bodies in a lumbar spine from a lateral approach. The device is expanded by the insertion of a plurality of wafers into the device in situ. The length of the device is configured to extend on the vertebral body endplate from pedicle to pedicle and to reside interiorly of the ring apophysis with at least a portion of the device resting on the area of increased bone density at the posterior portion of the endplate between the pedicles.

11 Claims, 7 Drawing Sheets

Related U.S. Application Data

(60) Provisional application No. 61/532,673, filed on Sep. 9, 2011.

(51) Int. Cl.
*A61B 17/02* (2006.01)
*A61F 2/28* (2006.01)
*A61F 2/30* (2006.01)

(52) U.S. Cl.
CPC ............... *A61F 2002/30843* (2013.01); *A61F 2002/30904* (2013.01)

(56) References Cited

U.S. PATENT DOCUMENTS 5,772,661 A 6/1998 Michelson
5,860,973 A * 1/1999 Michelson ......... A61B 17/1757 606/247
6,241,770 B1 * 6/2001 Michelson ............. A61F 2/446 623/17.11
6,395,034 B1 5/2002 Suddaby
6,595,998 B2 7/2003 Johnson et al.
7,749,269 B2 7/2010 Peterman et al.
7,763,078 B2 7/2010 Peterman et al.
7,776,095 B2 8/2010 Peterman et al.
7,918,981 B2 4/2011 Jing et al.
7,967,867 B2 6/2011 Barreiro et al.
8,715,351 B1 5/2014 Pinto
8,900,312 B2 12/2014 McLean et al.
2002/0183761 A1 12/2002 Johnson et al.
2003/0009224 A1 1/2003 Kuras
2003/0130739 A1 7/2003 Gerbec et al.
2003/0171812 A1 9/2003 Grunberg et al.
2003/0233145 A1 12/2003 Landry et al.
2004/0019356 A1 1/2004 Fraser et al.
2004/0030391 A1 2/2004 Ferree
2004/0073314 A1 4/2004 White et al.
2004/0133280 A1 * 7/2004 Trieu ........................ A61F 2/44 623/17.16
2006/0058807 A1 * 3/2006 Landry ................... A61F 2/447 606/90
2006/0217806 A1 * 9/2006 Peterman .............. A61F 2/4455 623/17.11
2006/0229629 A1 10/2006 Mazi et al.
2007/0270952 A1 11/2007 Wistrom et al.
2008/0140207 A1 * 6/2008 Olmos .................. A61F 2/4455 623/17.16
2008/0300598 A1 * 12/2008 Barreiro ................ A61F 2/4611 606/63
2009/0216331 A1 8/2009 Grotz et al.
2010/0063510 A1 * 3/2010 Arlet ......................... A61F 2/44 606/93
2010/0204798 A1 8/2010 Gerbec et al.
2010/0286784 A1 * 11/2010 Curran .................. A61F 2/4425 623/17.16
2010/0286785 A1 * 11/2010 Grayson ................ A61F 2/447 623/17.16
2010/0305706 A1 12/2010 Webb et al.
2011/0166657 A1 7/2011 Thalgott et al.
2011/0264219 A1 10/2011 Rouben
2011/0319999 A1 12/2011 O'Neil et al.
2012/0010715 A1 1/2012 Spann
2012/0010716 A1 1/2012 Spann
2012/0010717 A1 1/2012 Spann
2012/0022651 A1 1/2012 Akyuz et al.
2012/0059475 A1 * 3/2012 Weiman .................... A61F 2/44 623/17.16
2012/0136392 A1 5/2012 Keegan et al.
2012/0215313 A1 8/2012 Saidha et al.
2013/0166027 A1 6/2013 Bellas

OTHER PUBLICATIONS

H.B.S. Kemp et al.; "Anterior Fusion of the Spine for Infective Lesions in Adults"; The Journal of Bone and Joint Surgery; Nov. 1973; vol. 55B, No. 4, pp. 715-734; Stanmore, Middlesex, England.

* cited by examiner 58
54
65
44
62
64

44
t
58
54
62
60
56
64

44
54
56

58
54
65
64
62

56
44
58
60

LATERAL APPROACH EXPANDABLE SPINAL IMPLANT AND METHOD

CROSS-REFERENCES TO RELATED APPLICATIONS

This application is a divisional application of application Ser. No. 14/342,563, filed on Mar. 4, 2014, now abandoned, which is National Stage Application under 35 U.S.C. §371 of PCT International Application No. PCT/US2012/054055, filed Sep. 7, 2012, which claims priority to U.S. Provisional Patent Application No. 61/532,673, filed on Sep. 9, 2011, the entire contents of which are incorporated by reference herein.

FIELD OF THE INVENTION

The subject invention relates generally to the field of spinal implants and more particularly to expandable interbody fusion devices and methods for implanting such devices in a lateral approach.

BACKGROUND

Spinal implants such as interbody fusion devices are used to treat degenerative disc disease and other damages or defects in the spinal disc between adjacent vertebrae. The disc may be herniated or suffering from a variety of degenerative conditions, such that the anatomical function of the spinal disc is disrupted. Most prevalent surgical treatment for these conditions is to fuse the two vertebrae surrounding the affected disc. In most cases, the entire disc will be removed, except for a portion of the annulus, by way of a discectomy procedure. A spinal fusion device is then introduced into the intradiscal space and suitable bone or bone substitute material is placed substantially in and/or adjacent the device in order to promote fusion between two adjacent vertebrae.

Spinal fusion devices may be inserted during a spinal surgical procedure using an anterior, posterior, posterior lateral or extrapedicular approach. Certain spinal devices for achieving fusion using such approaches are also expandable so as to correct disc height between the adjacent vertebrae. Examples of expandable interbody fusion devices are described in U.S. Pat. No. 6,595,998 entitled "Tissue Distraction Device", which issued on Jul. 22, 2003 (the '998 Patent) and U.S. Pat. No. 7,967,867 entitled "Expandable Interbody Fusion Device", which issued on Jun. 28, 2011 (the '867 Patent). The '998 Patent and the '867 Patent each discloses sequentially introducing in situ a series of elongate inserts referred to as wafers in a percutaneous approach to incrementally distract opposing vertebrae to stabilize the spine and correct spinal height, the wafers including features that allow adjacent wafers to interlock in multiple degrees of freedom. The '998 Patent and the '867 Patent are both assigned to the same assignee as the present invention, the disclosures of both patents being incorporated herein by reference in their entirety.

Other spinal fusion devices may be inserted into the disc space using a lateral approach, as shown for example, in U.S. Pat. No. 7,749,269 which issued on Jul. 6, 2010 and is assigned on its face to Warsaw Orthopedic, Inc. (the '269 Patent) and U.S. Pat. No. 7,918,891 which issued Apr. 5, 2011 and is assigned on its face to NuVasive Inc. (the '891 Patent). The fusion devices described in both the '269 Patent and the '891 Patent are monolithic implants of fixed dimensions with neither having capability of expansion or tissue distraction once introduced into the intradiscal space. As such, the height of the implant upon insertion determines the final height of the corrected disc space. In addition, for implantation using a lateral approach, these implants are configured to be of length to be positioned in the disc space from one lateral side to the other such that the implant rests on the cortical rims of both opposing lateral sides of a vertebral body.

Consequently, there remains a need for an expandable interbody fusion device for insertion into the intradiscal space between opposing vertebrae using a lateral approach.

SUMMARY OF THE INVENTION

The present invention contemplates an expandable interbody fusion device configured for placement into the intradiscal space between vertebral bodies in a spine from a lateral approach to increase the disc height between vertebral bodies upon expansion and to stabilize the spine.

BRIEF DESCRIPTION OF THE DRAWING FIGURES

DETAILED DESCRIPTION

Figure 1:
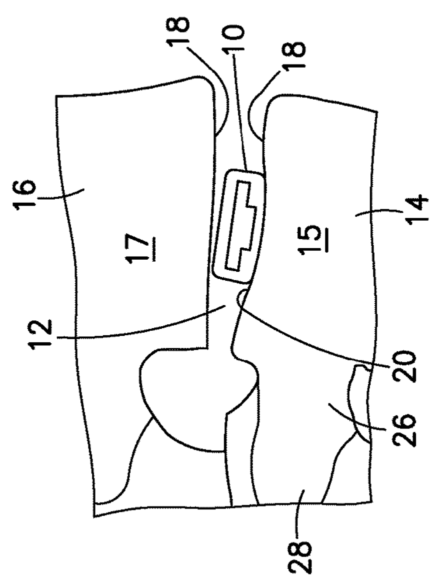
FIG. 1 is a side view of a portion of the lumbar spine showing an expandable device inserted from a lateral approach in an unexpanded condition.

For the purposes of promoting an understanding of the principles of the invention, reference will now be made to the drawing figures and the following written description. It is understood that no limitation to the scope of the invention is thereby intend. It is further understood that the present invention includes any alterations and modifications to the illustrated arrangements and further includes applications of principles of the invention as would normally occur one skilled in the art to which this invention pertains.

Figure 2:
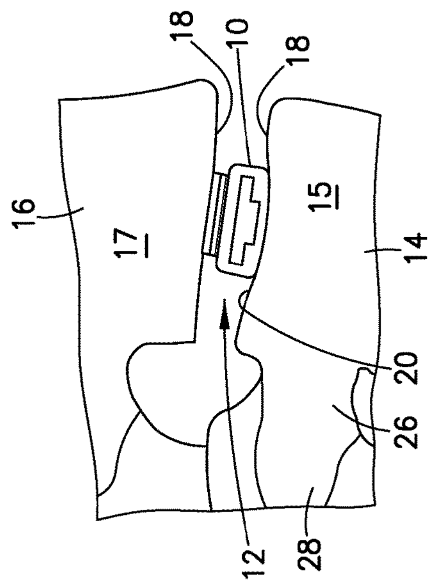
FIG. 2 is the view of FIG. 1 showing the expandable device expanded in situ.

Referring now to FIGS. 1 and 2 an expandable interbody fusion device 10 is shown as being implanted from the direct lateral approach into the intradiscal space 12 between two opposing vertebrae 14, 16. In FIG. 1, the device 10, described in further detail below, is introduced in an unexpanded condition. FIG. 2 illustrates the device 10 expanded in situ to distract the opposing vertebrae 14, 16 thereby correcting the height of the spine by increasing the intradiscal space 12 and stabilizing the spine by supporting the vertebrae 14, 16 for fusion.

Figure 3:
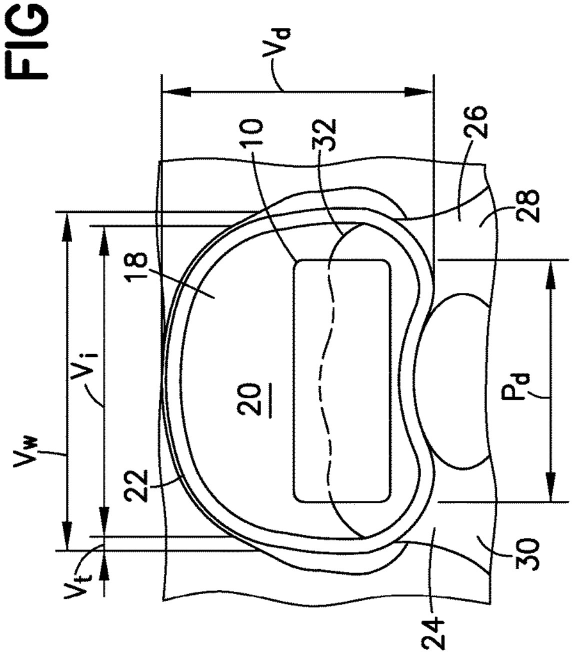
FIG. 3 is a sectional view of the intradiscal space showing the expandable insert of FIG. 1 resting on a region of increased bone density of the vertebral endplate between the pedicles.
Figure 4:
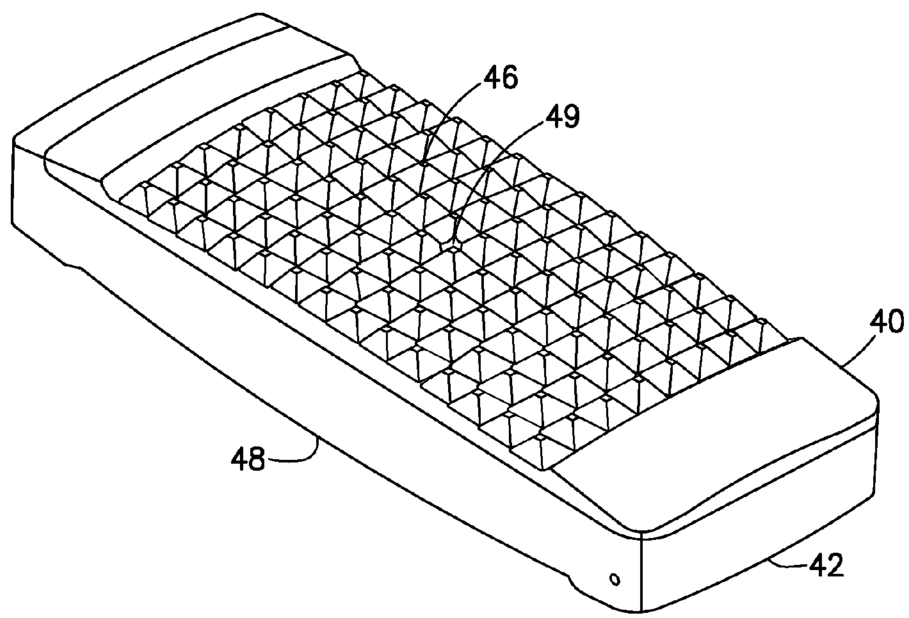
FIG. 4 is a top perspective front view of the unexpanded device of FIG. 1.
Figure 5:
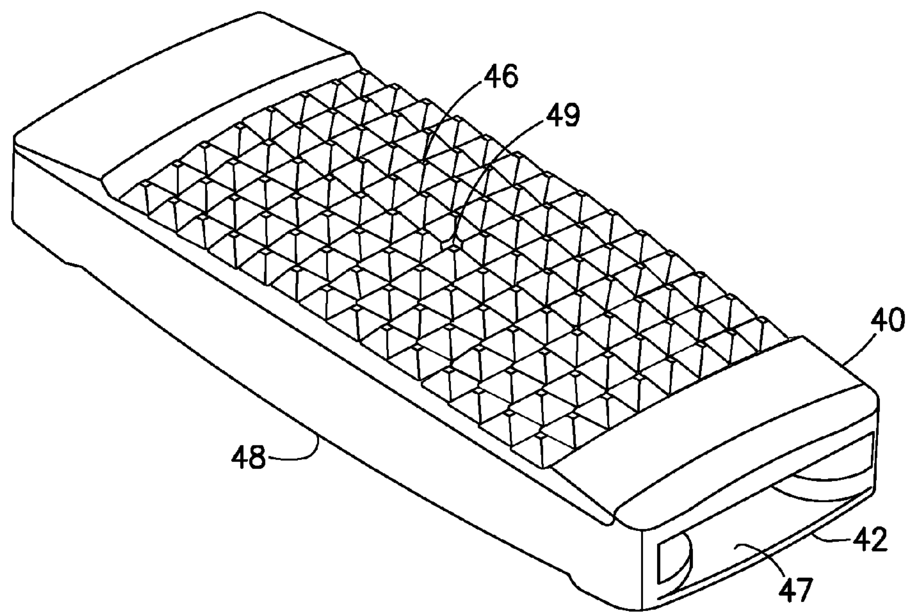
FIG. 5 is a top perspective rear view of the unexpanded device of FIG. 1.

Turning to FIG. 3, there is shown a preferred arrangement for placement of the expandable device 10 in the intradiscal space 12 using the lateral approach. As will be described hereinbelow in more detail, the device 10 is implanted with an insertion instrument in accordance with the disclosures of the '998 patent and the '867 patent, incorporated herein by reference in their entirety. Upon insertion into the intradiscal space 12 the device 10 is placed between the endplates 18 of the respective vertebral bodies 14, 16. Each vertebral body 14, 16 is defined by an outer wall 15, 17 respectively of relatively strong cortical bone which surrounds an interior (not shown) of relatively soft cancellous bone. The vertebral endplates 18 in the lumbar spine contain two separate anatomic elements, namely an interior plateau 20 surrounded by a rim or ring apophysis 22. The interior plateau 20 is slightly depressed, flat or slightly concave and is formed of relatively strong cartilage. The ring apophysis 22 is typically defined as the strong ring of cortical bone that exists on the periphery of the vertebral body coincident with the outer wall of cortical bone of the vertebral body.

At the posterior portion of each vertebral body 14, 16 there are two short, thick processes known as pedicles 24 and 26, which project dorsally, one on either side, from the superior part of the vertebral body at the junction of its posterior and lateral surfaces as shown in FIG. 3. The pedicles 24 and 26 connect the vertebral body 14 to the superior processes 28 and 30 that form the facet joints. Between the pedicles 24, 26 at the posterior margin of the respective endplates 18, there is an area 32 of increased bone density that is stronger than other parts of the vertebral body endplate 18. The posterior of the endplate 18 is stronger than anterior, the periphery is stronger than the center and the strongest portion is the posterolateral corners, where the vertebral body 14 meets the pedicles 24, 26, which may be up to twice the strength of the center of the endplate 18. In accordance with a particular arrangement of the insertion of the device 10 from the lateral approach, the device 10 is placed on the endplate 18 such that at least a portion of the device 10 rests on the area 32 with the length of the device 10 being configured such that the device 10 resides within the rim or ring apophysis 22, as depicted in FIG. 3. As such, the device 10 is preferably placed to reside on the posterior third of the endplate area.

With continued reference to FIG. 3, the average pedicle-to-pedicle dimensions, $P_d$ of the lumbar vertebrae L1 to L5 are set forth in Table 1 below. Other average anatomical dimensions of the lumbar vertebrae L1 to L5 are set forth in Table 1, wherein $V_w$ is the average width of vertebral body; $V_t$ is the average thickness of the ring apophysis 22; $V_i$ is the average interior dimension laterally across the width of the vertebral body between the opposing ring apophyses 22; and $V_d$ is the average depth of the vertebral body.

TABLE 1

| Dimension (mm) | L1 | L2 | L3 | L4 | L5 |
|---|---|---|---|---|---|
| $P_d$ | 30.6 | 31.4 | 33.6 | 37.9 | 45.9 |
| $V_w$ | 39.7 | 41.6 | 47.7 | 52.5 | 54.5 |
| $V_t$ | 3.0 | 3.0 | 3.0 | 3.0 | 3.0 |
| $V_i$ | 33.7 | 35.6 | 41.7 | 46.5 | 48.5 |
| $V_d$ | 29.0 | 31.1 | 34.6 | 38.0 | 37.6 |

Accordingly, considering the vertebral body dimensions set forth in Table 1 a device 10 having a length L ranging from about 31 mm to 46 mm would extend approximately from pedicle-to-pedicle consistent with the dimension, $P_d$ for the lumbar vertebrae L1 to L5. A device 10 having such a range of lengths would also preferably be less than the interior dimension, $V_i$. Further, the length L may be as great as approximately 48 mm and still satisfy these conditions.

Figure 6:
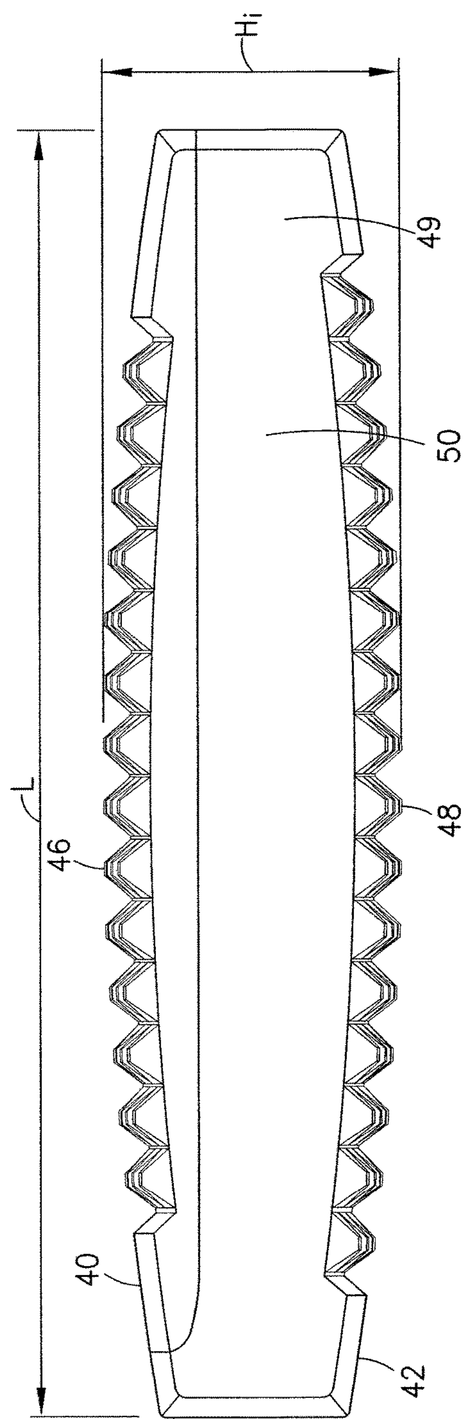
FIG. 6 is a side elevation view of the unexpanded device of FIG. 4.
Figure 7:
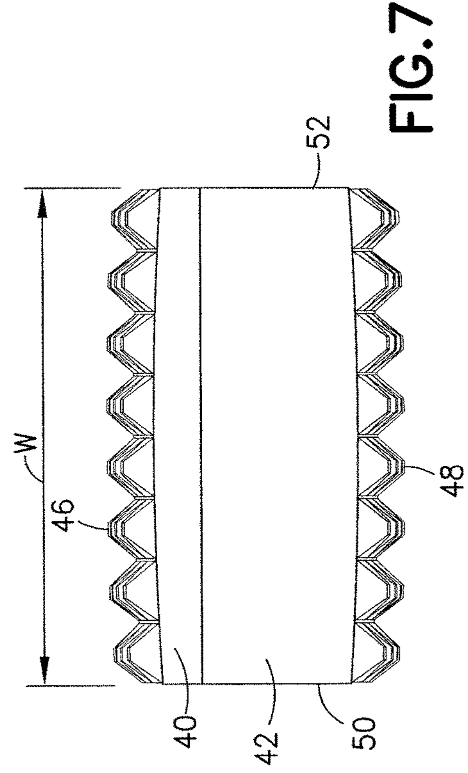
FIG. 7 is a front end view of the unexpanded device of FIG. 4.

Referring now to FIGS. 4-7, the expandable device 10 is shown in the unexpanded condition. The device 10 comprises a superior endplate 40, an inferior endplate 42 and a stack of interlocking wafers 44 described with reference to FIGS. 8-12 that are introduced sequentially between the endplates 40 and 42 through a channel 47 extending into the inferior endplate 42. Except for the dimensions of the device 10 that are configured herein for particular application using a lateral approach for insertion, the device 10 including the endplates 40 and 42 and wafers 44 are substantially the same, both structurally and functionally, as the endplates and wafers described in the '867 Patent, incorporated herein by reference in its entirety. Another difference of the device 10 over the device of the '867 Patent is that the device 10 in the configuration shown in FIGS. 4-7 is bi-convex, in that the endplates 40 and 42 each have convex upper and lower surfaces 46 and 48 respectively along the directions of both the length (FIG. 6) and width (FIG. 7). In addition, instead of a saw-tooth outer surface, the outer upper and lower surfaces 46 and 48 of device 10 comprise a pattern of truncated pyramids to firmly grip the endplates 18 of the opposing vertebral bodies 14 and 16. It should be appreciated that other gripping surfaces may also be used. Lastly, the device 10 comprises radiopaque markers 49 such as tantalum beads disposed, for example, on the upper and lower surfaces 46, 48 and on at least one of the sidewalls 50 and 52 of the inferior endplate 42 adjacent the front end of the device. The markers 49 assist the surgeon using fluoroscopic visualization in the placement of the device 10 during insertion into the intradiscal space 12 and to monitor the expansion of the device 10 upon the introduction of wafers 44.

As shown in FIG. 6, device 10 is elongate and has a length L defined as the maximum length along a lengthwise direction of device 10. Device 10 has an unexpanded height $H_i$ defined as the maximum height along the direction of the device 10 that extends between the vertebral bodies 14 and 16. The device 10 has a width W as shown in FIG. 7 that extends between the side walls 50 and 52, the width W being less than the length L and defined as the maximum width of the device 10.

Turning now to FIGS. 8-12, the details of wafers 44 are illustrated. As set forth in the '867 patent, each wafer 44 has an upper surface 54 and a low surface 56 that are generally planar so that the wafers 44 can form a stable stack within the device 10. The trailing end 58 has a downward-facing sloped surface 60 that corresponds angularly to an upward-facing sloped surface 62 on the leading end 64 of the wafer 44. The two sloped surfaces help displace an earlier inserted wafer 44 upon introduction of a new wafer 44. More specifically, when a wafer 44 is inserted into channel 47 of the inferior endplate 42 (FIG. 5), the downward-facing sloped surface 60 is lifted by contact with the upward-facing sloped surface 62 of a newly inserted wafer 44. Incremental expansion of the device 10 along the direction of its height is effected by the individual consecutive introduction of a plurality of wafers 44 until a suitable increase in device height is achieved.

Figures 8, 9, 10, 11, 12:
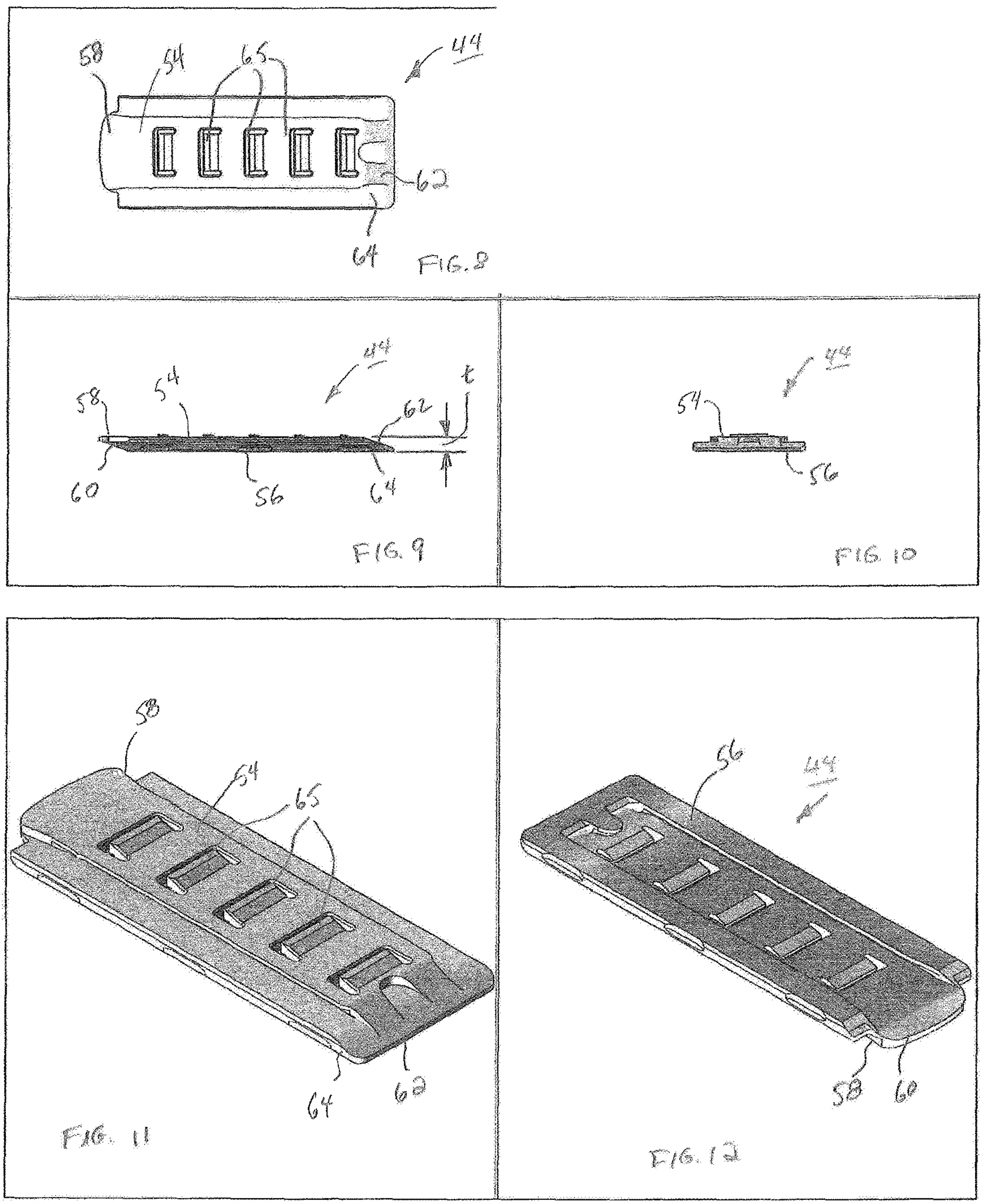
FIG. 8 is a top plan view of a wafer insertable into the expandable device of FIG. 1 to expand the device.
FIG. 9 is a side elevation view of the wafer of FIG. 8.
FIG. 10 is a front interview of the wafer of FIG. 8.
FIG. 11 is a top perspective front view of the wafer of FIG. 8.
FIG. 12 is a bottom perspective view of the wafer of FIG. 8.
Figure 13:
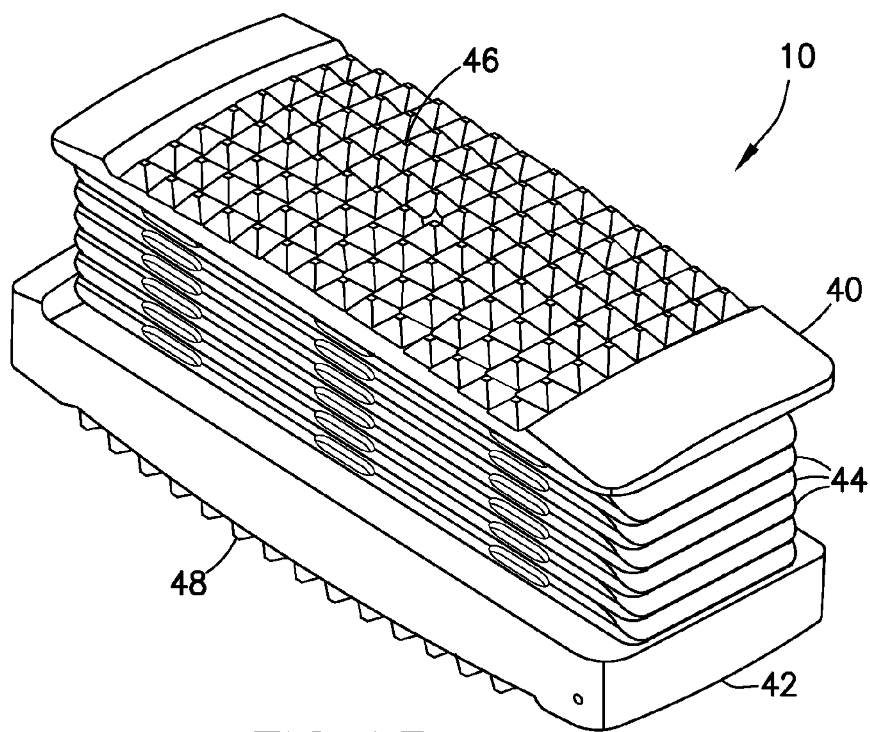
FIG. 13 is a top perspective front view of expanded device of FIG. 2.
Figure 14:
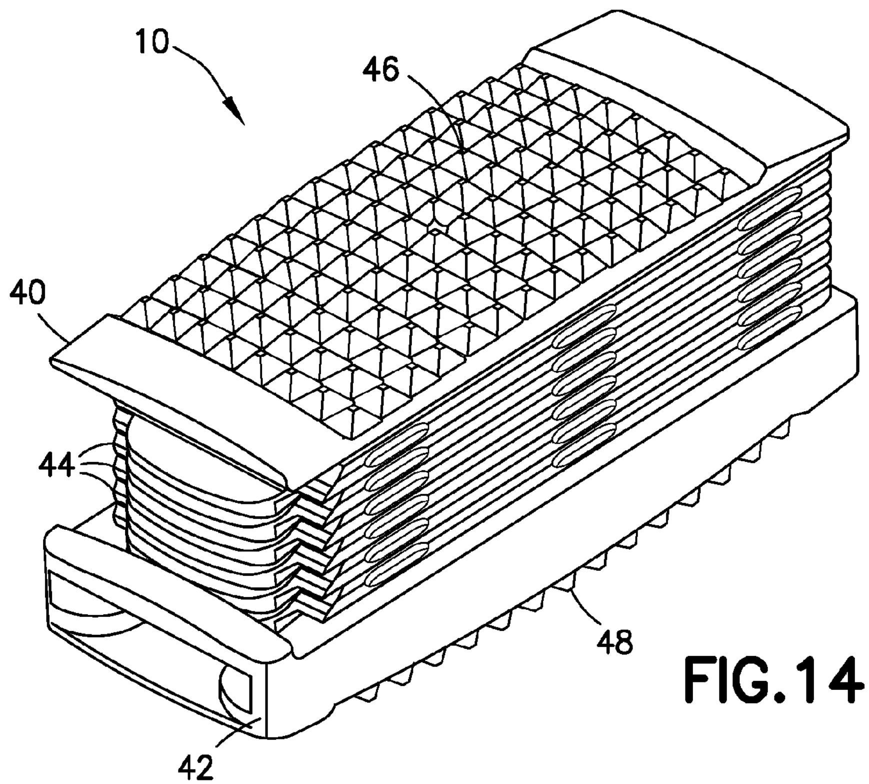
FIG. 14 is a top perspective rear view of expanded device of FIG. 2.
Figure 15:
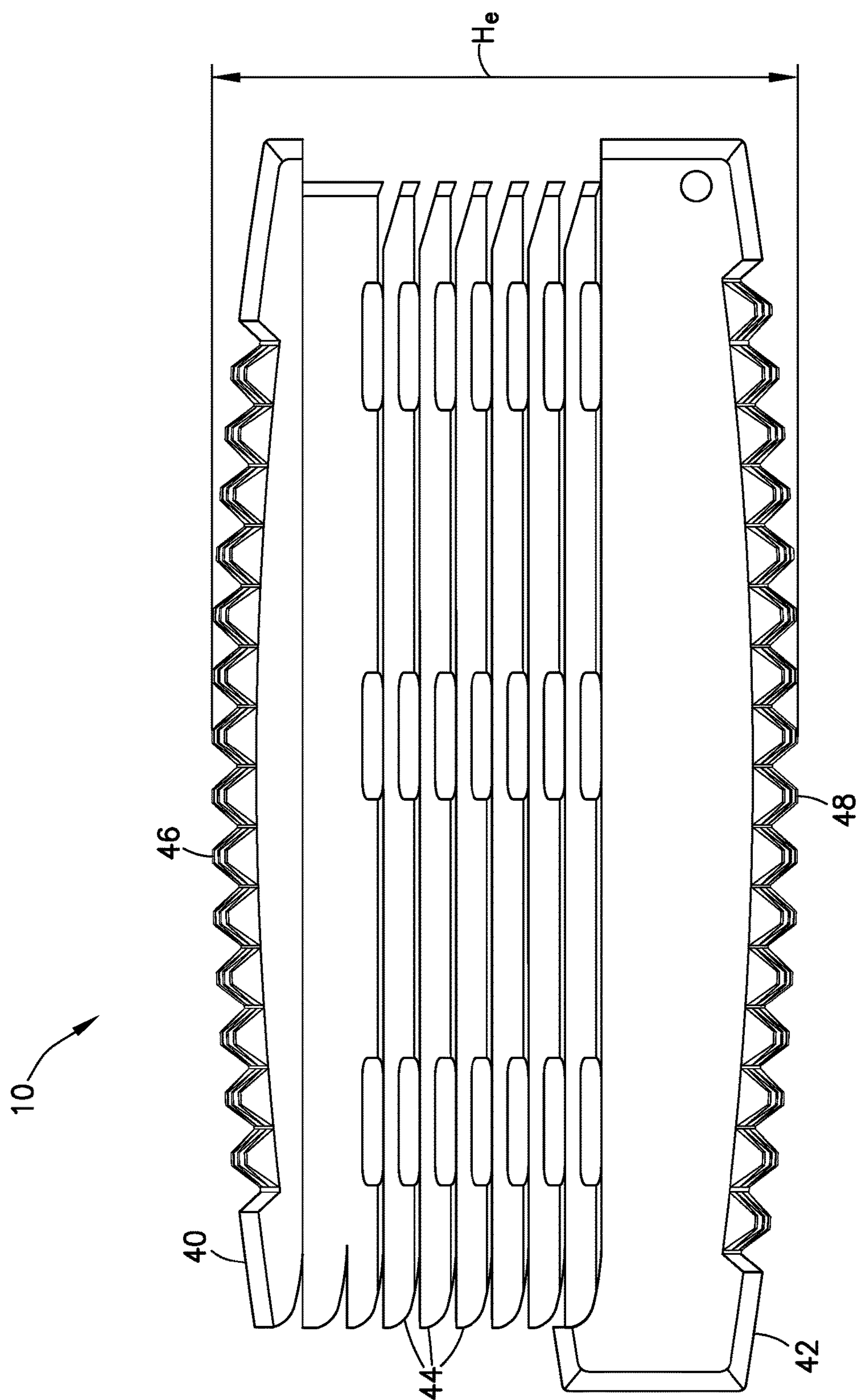
FIG. 15 is a side elevation view of expanded device FIG. 13.

As also described in the '867 patent, each wafer 44 includes features to interlock adjacent wafers in multiple degrees of freedom. One particular feature includes a series of resiliently flexible prongs 65 that project outwardly above the upper surface 54 of the wafer 44 as shown in FIGS. 8 and 11. Although five prongs 65 are shown, fewer or more may be used. Features are also described in the '867 patent to interlock the upper-most wafer 44 in the stack to the lower surface of the superior endplate 40 and the stack of wafers 44 to the inferior endplate 42. As illustrated in FIG. 9, each wafer 44 has a thickness t defined as the maximum dimension between the upper surface 54 and the lower surface 56. While one particular arrangement of effecting expansion as described herein is the sequential introduction of individual wafers 44, it should be appreciated that other expansion mechanisms may be applicable. For example, an expansion mechanism may comprise a cam element, cooperating inclined surfaces or a threaded wedge structure to cause separating movement of the superior endplate 40 and the inferior and plate 42 and hence increase in the spacing between the upper surface 46 and the lower surface 48 of the device 10. Insertion of separate individual wafers 44, however, provides control over the expansion capability including greater flexibility for the surgeon to monitor the stability of the device upon expansion. As illustrated in FIGS. 13-15, device 10 is shown in the expanded condition with a stack of wafers 44 having been inserted between superior endplate 40 and the inferior endplate 42, thereby increasing the height of the device 10 to an expanded height $H_e$.

Figure 16:
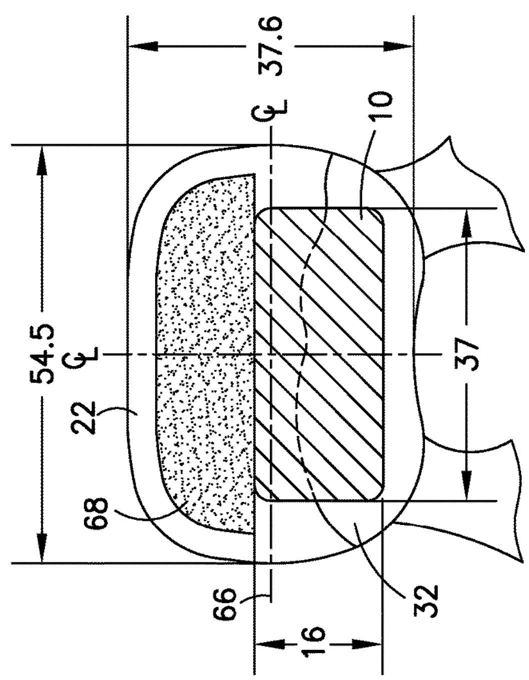
FIG. 16 is a schematic representation of the placement of the device of FIG. 3 showing the disposition of graft material and dimensions in accordance with a particular arrangement.

Referring now to FIG. 16, the method of inserting the expandable device 10 from the lateral approach is described. The direct lateral approach involves creating access by navigating through the psoas muscle and past the lumbar plexus which receives nerve contributions at lumbar levels. For such navigation, surgeons employ appropriate intraoperative monitoring techniques and instruments. Such instruments may include monopolar probes, tissue dilators and retractors. One technique for such lateral access is described in U.S. Pat. No. 4,545,374 issued to Robert E. Jacobson on Oct. 8, 1985 and entitled "Method and Instruments for Performing a Percutaneous Diskectomy" (the '374 Patent). Monitoring instruments and tissue dilators are also described in co-pending, commonly assigned U.S. Provisional Patent Application No. 61/532,668, entitled "Apparatus for Dilating Bodily Tissue and for Monitoring Neural Activity in the Dilated Bodily Tissue", filed on even date herewith (the '668 Application). The '374 Patent and the '668 Application are incorporated herein by reference in their entireties.

Having satisfactorily achieved a direct lateral access surgical corridor through the tissue down to the disc space, a discectomy is performed to provide appropriate space for introduction of the expandable device 10. In some instances, pre-distraction of the disc space may be required to facilitate the introduction of the device 10, it being understood that such pre-distraction is not the final distraction desired to achieve corrected disc height and spinal correction. The device 10 is inserted by an insertion instrument as described in the '867 Patent which supports the device 10 upon and during insertion and releases the device 10 once expanded. Where a retractor is used with, for example, a plurality of blades to create a relatively large access corridor for enhanced visual observation, the device 10 may be inserted through the retractor which holds tissue apart adjacent the surgical site. Because of the relatively small profile of the unexpanded device 10, the retractor may not be necessary and instead the device 10 may be introduced percutaneously through a cannula of fixed dimension which would be placed over the last and largest tissue dilators with less tissue disruption.

As depicted in FIG. 16, the device 10 is placed in the intradiscal space 12 such that at least a portion of device 10 rests on the area 32 of increased bone density between the pedicles, with the length L being configured such that device 10 extends at least the pedicle-to pedicle dimension and resides within the ring apophysis 22. In a preferred placement, the device 10 preferably resides offset posteriorly from the transverse center line 66 and approximately on the posterior third of the endplate 18. In one particular arrangement, an unexpanded device 10 is configured to have a length L of about 37 mm, a width W of about 16 mm and unexpanded height $H_i$ of about 8 mm. In the illustration of FIG. 16, the device 10 is placed in the intradiscal space 12 between vertebral bodies L4 and L5 with the dimensions being shown for the 15 vertebral body, as set forth in Table 1 above. Individual wafers 44 are introduced to expand the device 10 with each wafer 44 having a thickness t of about 1 mm. While it is desirable to increase the height of the device 10 by any amount, it is preferable to increase the height $H_e$ at least 50% up to about 12 mm which would be accomplished by adding at least four such wafers 44. Further height increases up to about 17 mm may be achieved by adding nine wafers. The desired height and stability of the spine is determined by the surgeon based upon sensory feedback upon insertion of wafers 44. While the dimensions of the particular arrangement are illustrative, it should be appreciated that other suitable device lengths, widths and heights may be contemplated. As such, the width W of device 10 may range from about 14 mm to about 20 mm while the length L as noted hereinabove may range from about 31 mm to 48 mm for application in the lumbar spine region from L1 to L5.

Having expanded the device 10, suitable bone filler or bone graft 68 may be inserted into the intradiscal space 12. As depicted in FIG. 16, the graft 68 may be placed adjacent the device 10 toward the anterior direction. A suitable graft insertion instrument to inject graft under pressure to stress load the graft against the vertebral endplates 18 after the device 10 is expanded is desirable. In some instances some graft 68 may be placed prior to insertion of device 10.

Figure 17:
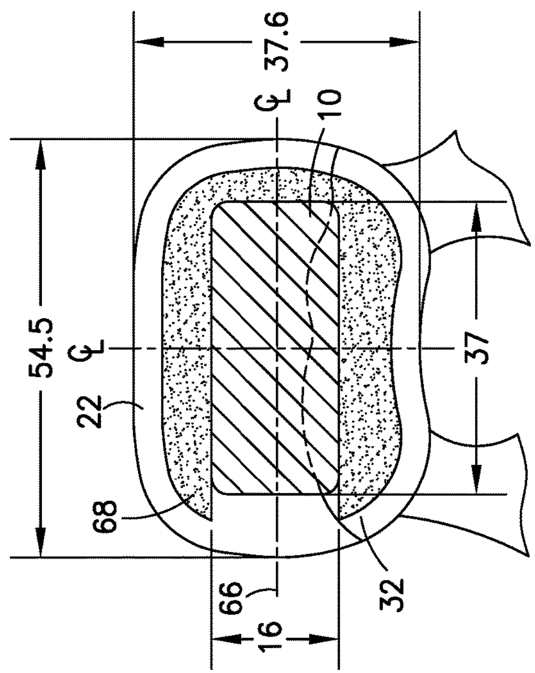
FIG. 17 is a schematic representation similar to FIG. 16 showing the placement of the expandable device substantially along the lateral centerline of the vertebral body.

By reference to FIG. 17, it can also be seen that the device 10 may be inserted into the intradiscal space 12 generally along the transverse center line 66. While a portion of the device 10 may rest on the increased bone density area 32, it is likely to be less than that of FIG. 16. Bone filler or bone graft 70 may be suitably injected under pressure prior to the insertion of device 10 and then subsequent to device expansion adjacent device 10 on both the anterior and posterior sides.

Figure 18:
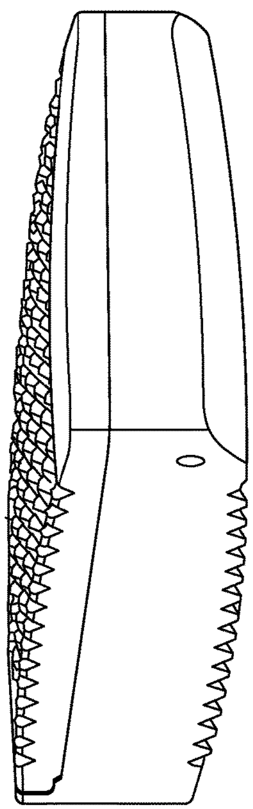
FIG. 18 is a front perspective view of an unexpanded expandable device having a lordotic angle and insertable from the lateral approach.

Having described the particular arrangements of the device 10 and method of placement, it should be understood that other variations may be contemplated. For example, as shown in FIG. 18, an expandable device 72 similar to device 10 may be configured to not only be bi-convex but also to provide a lordotic angle on the order of about 6 degrees or other suitable angle. Device 72 may maintain such a lordotic angle upon expansion or where the device is substantially freely introduced into the intradiscal space 12, create lordosis upon expansion whereby the intradiscal space at the anterior portion of the spine is greater than at the posterior portion. Accordingly, the arrangements described herein are intended to be illustrative and not limiting.

What is claimed is:

1. A method of inserting an expandable interbody fusion device from the lateral approach into the intradiscal space of the lumbar spine, the intradiscal space being divided by a transverse centerline extending across the lateral width of said intradiscal space that defines an anterior portion and a posterior portion, comprising the steps of:

providing an access corridor to the spine from the lateral approach;

providing an elongate expandable device having a length and a width, said length being less than the lateral width of the vertebral endplate interiorly between the peripheral ring apophysis and not less than the pedicle-to pedicle spacing of the vertebral body;

inserting said device into the intradiscal space between opposing vertebral bodies entirely within the interior of said ring apophysis of said endplate with at least a portion of the width of said device being disposed in the anterior portion of said intradiscal space and a greater portion of the width of said device being disposed in the posterior portion of said intradiscal space and residing on the area of endplate increased bone density at the posterior portion of the endplates between the pedicles; and then expanding the expandable device in situ to increase the height of the intradiscal space and stabilize the spine.

2. The method of claim 1, wherein said elongate expandable device comprises a superior endplate, an inferior endplate and an expansion structure therebetween, and wherein said expansion structure is expanded to increase the height of said device.

3. The method of claim 2, wherein said expansion structure comprises a plurality of elements that are introduced into said device individually consecutively to form a stack of elements between said superior endplate and said inferior endplate.

4. The method of claim 2, wherein the height of said device is increased from an unexpanded height to an expanded height, said expanded height being at least 50% greater than said unexpanded height.

5. The method of claim 1, further including the step of nerve monitoring during the creation of said access corridor.

6. The method of claim 5, further including the step of dilating said access corridor.

7. The method of claim 6, further including the step of enlarging the access corridor, and wherein said device is inserted through said enlarged access corridor.

8. The method of claim 1, wherein a bone filler is inserted into said intradiscal space adjacent said expanded device.

9. The method of claim 8, wherein said bone filler is a bone graft and is injected under pressure to stress load the bone graft against the vertebral endplates of opposing vertebral bodies communicating with said intradiscal space.

10. The method of claim 9, wherein said bone graft is placed prior to insertion of device.

11. The method of claim 9, wherein after insertion of said device said bone graft is placed adjacent the device only in said anterior portion of said intradiscal space.

* * * * *